(12) United States Patent
Nakamura et al.

(10) Patent No.: US 7,880,873 B2
(45) Date of Patent: Feb. 1, 2011

(54) DROPLET DISCHARGE DEVICE

(75) Inventors: Tomonori Nakamura, Nagano (JP); Shoji Tsutsui, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 6 days.

(21) Appl. No.: 12/323,004

(22) Filed: Nov. 25, 2008

(65) Prior Publication Data

US 2009/0168056 A1 Jul. 2, 2009

(30) Foreign Application Priority Data

Dec. 26, 2007 (JP) ............................. 2007-334870

(51) Int. Cl.
*G01N 21/00* (2006.01)
(52) U.S. Cl. ........................... 356/237.1; 347/7; 347/19
(58) Field of Classification Search ... 356/237.1–237.5, 356/239.1–239.4; 347/9, 19, 16, 7, 47
See application file for complete search history.

(56) References Cited

U.S. PATENT DOCUMENTS 5,966,212 A * 10/1999 Hendler et al. ........... 356/239.3
7,092,082 B1 * 8/2006 Dardzinski ............... 356/237.5
7,399,048 B2 * 7/2008 Inoue ......................... 347/19
2005/0018182 A1 * 1/2005 Hyun et al. .............. 356/237.4

FOREIGN PATENT DOCUMENTS

| CN | 1916610 A | | 2/2007 |
| JP | 50-39188 U | | 11/1975 |
| JP | 405149887 A | * | 6/1993 |
| JP | 2001-159613 A | | 6/2001 |
| JP | 2007-40862 A | | 2/2007 |
| JP | 2007-085960 A | | 4/2007 |

* cited by examiner

*Primary Examiner*—Hoa Q Pham
(74) *Attorney, Agent, or Firm*—Global IP Counselors, LLP

(57) ABSTRACT

A pattern formation device is for forming a pattern on a substrate includes first and second foreign matter detection sensors. Each of the first and second foreign matter detection sensors includes a light projecting unit and a light receiving unit disposed across a transport path of the substrate from the first light projecting unit. The light projecting unit is configured and arranged to emit a detection light along an upper surface of the substrate. The light receiving unit being configured and arranged to receive the detection light to detect foreign matter on the substrate based on an amount of the detection light received by the light receiving unit. The light projecting units of the first and second foreign matter detection sensors are disposed on opposite sides of the transport path.

7 Claims, 6 Drawing Sheets

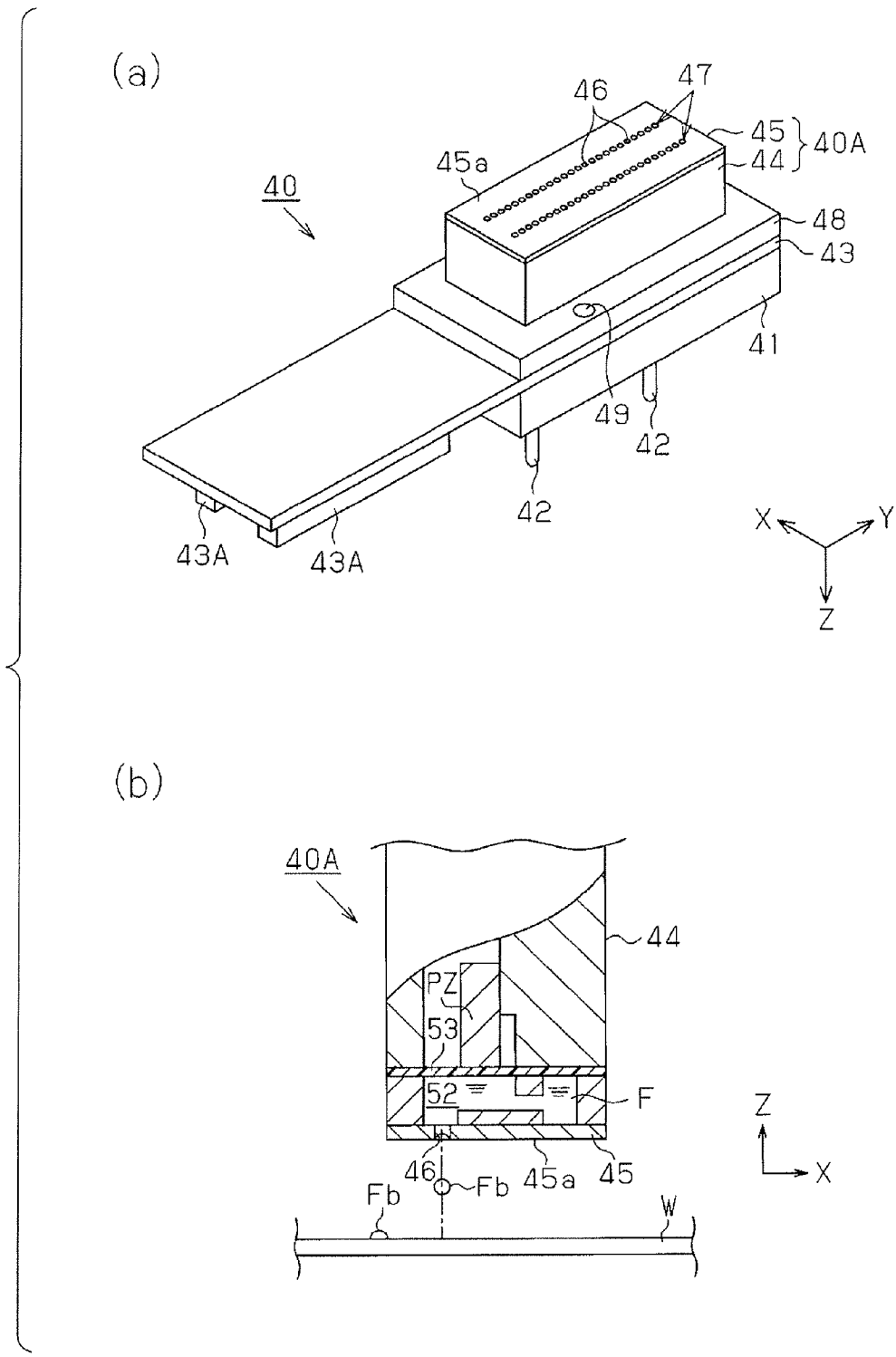
F I G. 3

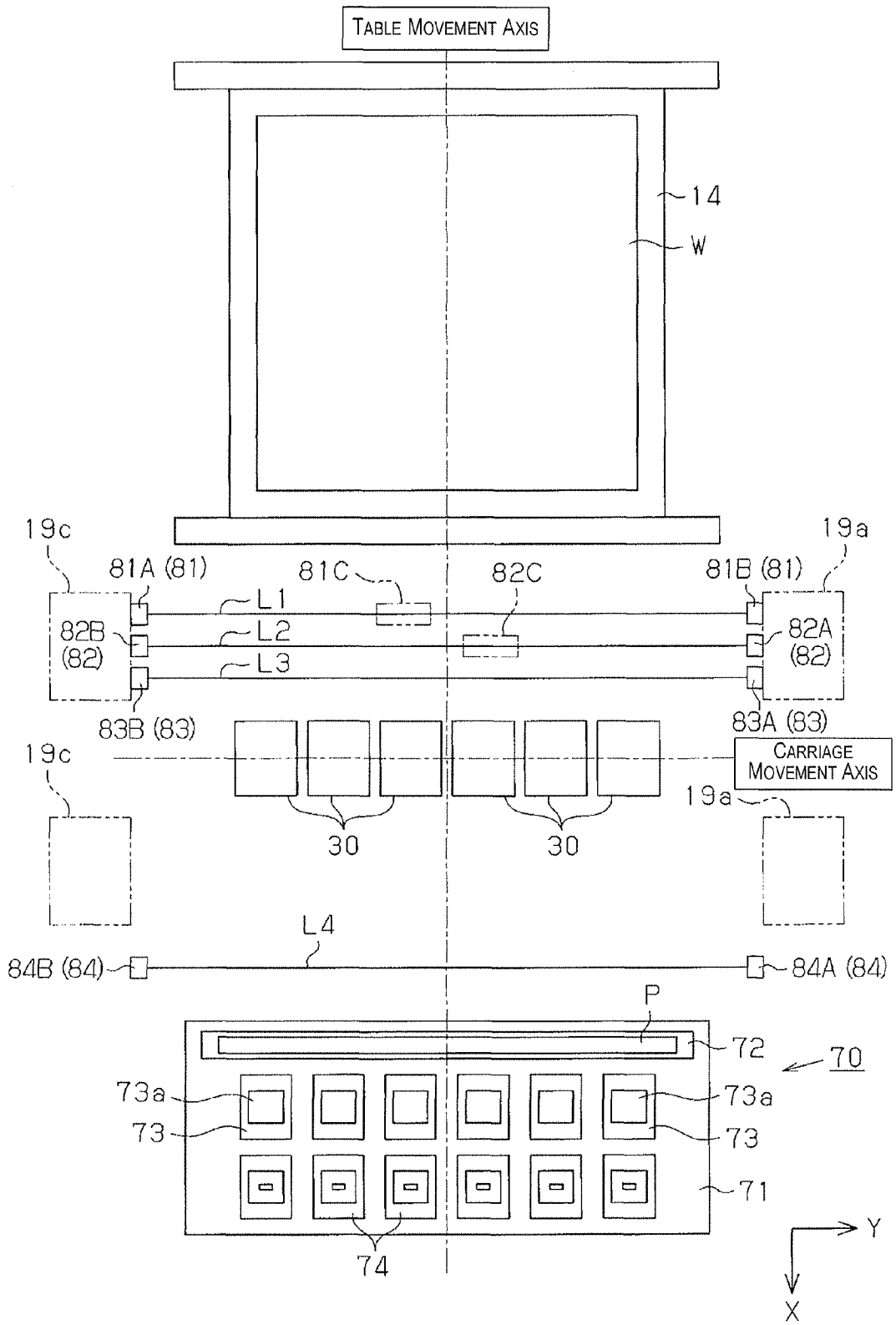
F I G. 4

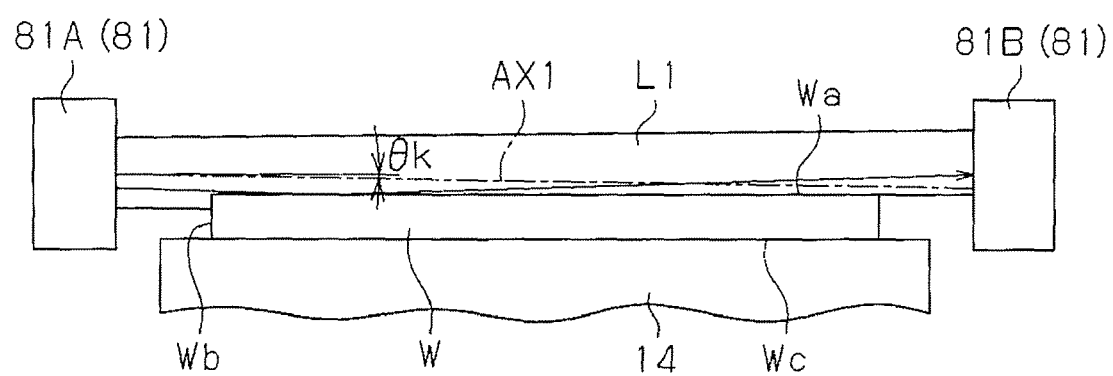
F I G. 5

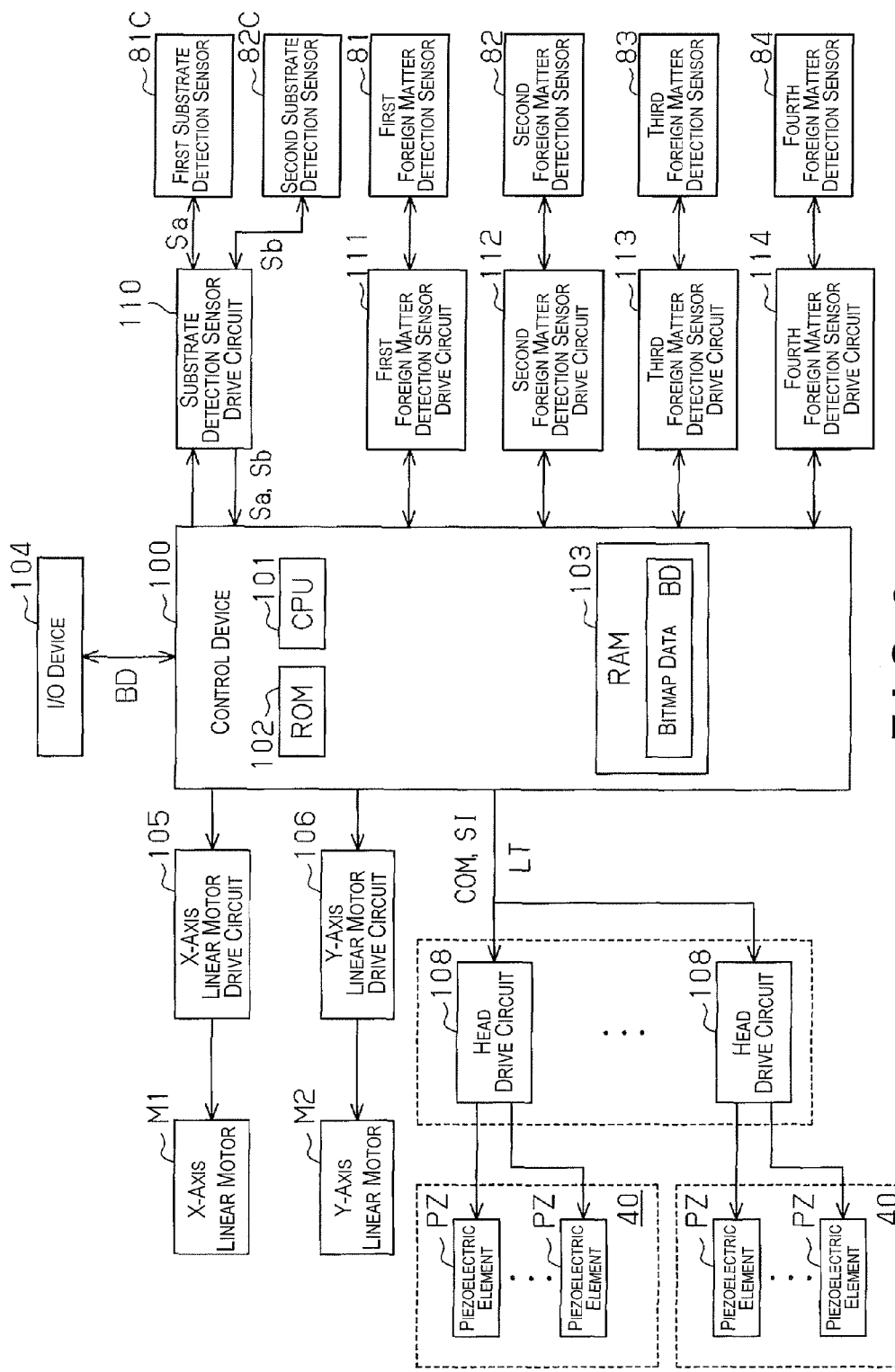
F I G. 6

DROPLET DISCHARGE DEVICE

CROSS-REFERENCE TO RELATED APPLICATIONS

This application claims priority to Japanese Patent Application No. 2007-334870 filed on Dec. 26, 2007. The entire disclosure of Japanese Patent Application No. 2007-334870 is hereby incorporated herein by reference.

BACKGROUND

1. Technical Field

The present invention relates to a pattern formation device.

2. Related Art

An inkjet device, i.e., a droplet discharge device for forming and discharging functional liquid as droplets is generally known as a device for forming a desired pattern on a substrate using the functional liquid. The droplet discharge device forms a pattern by depositing droplets of functional liquid discharged from a droplet discharge head in arbitrary locations on a substrate while the substrate mounted on a stage and the droplet discharge head for forming and discharging functional liquid as droplets is moved in a relative fashion in a two-dimensional direction.

A functional liquid is supplied from a separately disposed tank, and the droplet discharge head temporarily stores the functional liquid thus supplied in an internally disposed ink chamber (cavity). The functional liquid stored in the ink chamber is formed into droplets and discharged from a large number of nozzle holes formed in a nozzle plate that is disposed so as to face the stage.

In recent years, multiple-carriage-type droplet discharge devices are known in which a plurality of droplet discharge heads is mounted on a single carriage and a plurality of such carriages is mounted on the device. Such a droplet discharge device is used in manufacturing large-screen color filters and in other applications, and the drawing speed is improved by simultaneously discharging droplets from the plurality of carriages.

When the droplet discharge device is forming a pattern on the substrate, a platen gap, which is a space between the droplet discharge head and the nozzle plate, is very small, e.g., 0.3 mm. Therefore, various problems occur when dust or other foreign matter is deposited on the substrate. An example of such a problem is that the foreign matter comes into contact with the droplet discharge head when foreign matter is deposited on the upper surface of the substrate mounted on the stage, and the substrate and droplet discharge head are damaged. Another example of such a problem is that the substrate in the area where the foreign matter is deposited on the lower surface of the substrate increase in height in relation to the stage, the substrate and the droplet discharge head make contact, and the substrate is damaged.

Japanese Laid-open Patent Application No. 2007-85960 discloses a foreign matter detection device that proposes a method for solving such problems, wherein a light projecting unit and a light receiving unit are provided, a substrate is passed between the light projecting unit and the light receiving unit, detection light emitted from the light projecting unit along the upper surface of the substrate is received by the light receiving unit, and foreign matter deposited on the substrate is detected based on the amount of light received by the light receiving unit.

SUMMARY

However, in the method described in the above mentioned publication, the detection light emitted from the light projecting unit is diffused as the light nears the light receiving unit in the case that the substrate is a large glass substrate used in the manufacture of a large-screen color filter. The accuracy for detecting foreign matter positioned in the area near the light receiving unit on the glass substrate is reduced when the detection is diffused. Therefore, foreign matter having the same size that would normally be detected cannot be detected depending on the position (the distance from the light projecting unit) of the foreign matter. In other words, when the substrate is passed directly below the droplet discharge head, the droplet discharge head, the substrate, or the like is occasionally damaged despite the fact that foreign matter has not been detected.

Also, droplet discharge devices have been used in practice in which an inspection unit for detecting droplets discharged from the droplet discharge head is provided, being moveably disposed directly below the droplet discharge head. When the inspection unit is moved directly below the droplet discharge head, the droplet discharge head is occasionally damaged by a foreign matter (a tool or the like) left behind by a worker during maintenance of the inspection unit.

The present invention was contrived in order to solve the problems described above, and an object of the present invention is to provide a pattern formation device for preventing foreign matter from damaging the droplet discharge head and the substrate.

A pattern formation device according to a first aspect is provided for forming a pattern on a substrate by discharging a functional liquid as droplets from a plurality of nozzles of a droplet discharge head mounted to a carriage with the nozzles being aligned in a sub-scanning direction orthogonal to a main scanning direction while the substrate disposed on a transport table is moved along a transport path in the main scanning direction. The pattern formation device includes a first foreign matter detection sensor and a second foreign matter detection sensor. The first foreign matter detection sensor includes a first light projecting unit and a first light receiving unit disposed across the transport path from the first light projecting unit. The first light projecting unit is configured and arranged to emit a first detection light along an upper surface of the substrate and the first light receiving unit being configured and arranged to receive the first detection light to detect foreign matter on the substrate based on an amount of the first detection light received by the first light receiving unit. The second foreign matter detection sensor includes a second light projecting unit and a second light receiving unit disposed across the transport path from the second light projecting unit. The second light projecting unit is configured and arranged to emit a second detection light along the upper surface of the substrate and the second light receiving unit being configured and arranged to receive the second detection light to detect foreign matter on the substrate based on an amount of the second detection light received by the second light receiving unit. The first light projecting unit and the second light projecting unit are disposed on opposite sides of the transport path.

In accordance with the pattern formation device of the present invention, a second foreign matter detection sensor in which the direction of the detection light is opposite that of the first detection light is provided, whereby foreign matter deposited in an area in which the first detection light of the first foreign matter detection sensor is diffused and the accuracy of detecting foreign matter is reduced, i.e., in an area near the first light receiving unit of the substrate when, for example, the substrate is large, can be detected with good precision by the second foreign matter detection sensor. In other words, foreign matter can be detected with good precision in all areas of the substrate by the cooperative operation of the first and second foreign matter detection sensors. As a result, damage to the droplet discharge head and the substrate caused by foreign matter deposited on the substrate can be prevented by stopping the transport operation of the transport table when foreign matter is detected, for example.

In the pattern formation device, the first and second foreign matter detection sensors are preferably arranged so that optical axes of the first and second detection lights are sloped toward the substrate.

In accordance with the pattern formation device, the amount of light received by the corresponding light receiving unit can be increased by reflecting a portion of the detection light emitted from each light projecting unit onto the substrate. Therefore, the contrast between portions in which foreign matter is not deposited and portions in which foreign matter is deposited can be increased in the light receiving unit for receiving each of the detection lights when foreign matter is deposited on the substrate. As a result, foreign matter deposited on the substrate can be detected with good precision.

The pattern formation device preferably has a first substrate detection sensor, a second substrate detection sensor, and a foreign matter detection sensor control unit. The first substrate detection sensor is configured and arranged to detect that the substrate is positioned directly below an optical axis of the first detection light. The second substrate detection sensor is configured and arranged to detect that the substrate is positioned directly below an optical axis of the second detection light. The foreign matter detection sensor control unit is configured to control an operation of the first foreign matter detection sensor based on a detection signal from the first substrate detection sensor, and to control an operation of the second foreign matter detection sensor based on a detection signal from the second substrate detection sensor.

In accordance with the pattern formation device, the first detection light is emitted from the first light projecting unit only when the substrate is position directly below the optical axis of the first detection light, for example. Also, the second detection light is emitted from the second light projecting unit only when the substrate is position directly below the optical axis of the second detection light. In other words, a portion of each of the detection lights cannot be reflected on the substrate, and the first and second foreign matter detection sensor can be stopped when the amount of light received by each light receiving unit is reduced. Therefore, foreign matter detection errors caused by a reducing the amount of light received by the light receiving unit can be prevented when a substrate is not present directly below the detection light.

The pattern formation device preferably has a transport table foreign matter detection sensor configured and arranged to detect foreign matter on an upper surface of the transport table.

In accordance with the pattern formation device, the transport table foreign matter detection sensor can detect tools, and other foreign matters left behind during maintenance of the transport stage, for example. As a result, damage to the carriage (droplet discharge head) and the substrate caused by foreign matters deposited on the upper surface of the substrate can be prevented by stopping the transport operation of the transport table when the transport table foreign matter detection sensor has detected foreign matter, for example.

The pattern formation device preferably has an inspection unit and an inspection unit foreign matter detection sensor. The inspection unit is configured and arranged to reciprocally move in the main scanning direction independent from the transport table directly below the droplet discharge head to inspect conditions of the droplets discharged from the droplet discharge head. The inspection unit foreign matter detection sensor is configured and arranged to detect foreign matter in the inspection unit.

In accordance with the pattern formation device, tools and other foreign matter left behind during maintenance of the detection unit can be detected, for example, prior to moving the detection unit directly below the carriage (droplet discharge head). As a result, damage to the carriage (droplet discharge head) caused by foreign matter on the inspection unit can be prevented.

BRIEF DESCRIPTION OF THE DRAWINGS

Referring now to the attached drawings which form a part of this original disclosure:

FIG. 3 includes diagrams (a) and (b) with the diagram (a) being a perspective view of a droplet discharge head as seen from a substrate stage, and the diagram (b) being a partial cross-sectional view of a pump part of the droplet discharge head according to the embodiment of the present invention;

FIG. 4 is a schematic plan view showing an arrangement of each foreign matter detection sensor according to the embodiment of the present invention;

FIG. 5 is a schematic elevational view showing a state in which a first foreign matter detection sensor has emitted a first detection light according to the embodiment of the present invention; and FIG. 6 is a block diagram for describing the control system of the droplet discharge device according to the embodiment of the present invention.

DETAILED DESCRIPTION OF EXEMPLARY EMBODIMENTS

An embodiment of the pattern formation device in which the present invention has been implemented is described below with reference to the diagrams.

Figure 1:
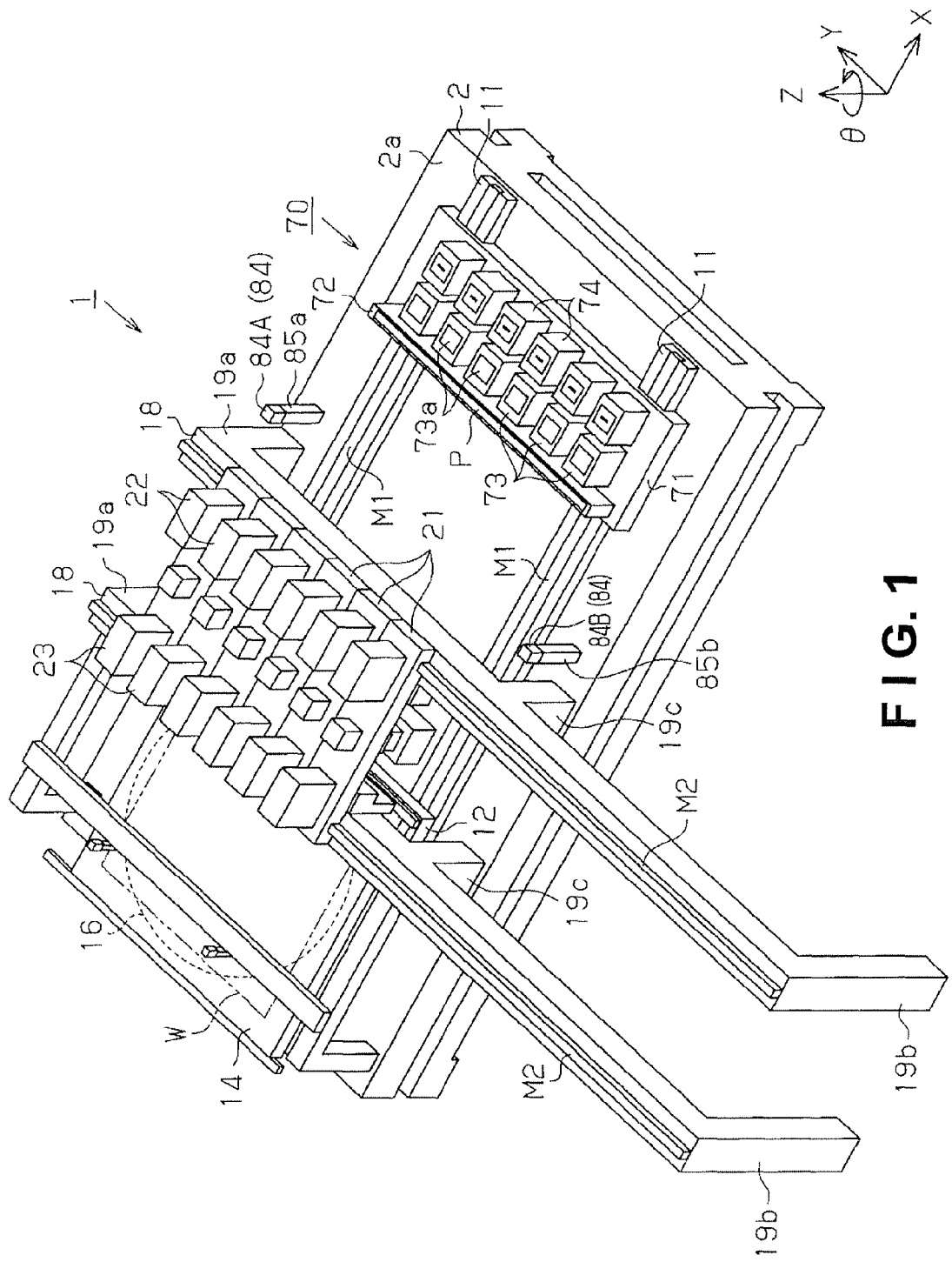
FIG. 1 is a perspective view of a pattern formation device according to an embodiment of the present invention.

FIG. 1 shows a schematic configuration of a droplet discharge device 1 as a pattern formation device for forming a red, green, and blue color filter on a glass substrate on which a black matrix has been formed. The droplet discharge device 1 has a base 2 extending in the main scanning direction (X-axis direction) on the surface of a floor, a pair of X-axis guide rails 11 is laid in the main scanning direction (X-axis direction) on the upper surface 2a of the base, and an X-axis moving table 12 constituting a transport table is mounted on the pair of X-axis guide rails 11, as shown in FIG. 1. The X-axis moving table 12 is mounted so as to be capable of movement in the main scanning direction along the X-axis guide rails 11. An X-axis linear motor M1 is provided to the pair of X-axis guide rails 11, and the X-axis linear motor M1 moves the X-axis moving table 12 mounted on the pair of X-axis guide rails 11 in a reciprocating fashion in the X-axis direction via a pneumatic slider (not shown).

In FIG. 1, the main scanning direction is the X-axis direction, the sub scanning direction orthogonal to the main scanning direction (X-axis direction) is the Y-axis direction, the direction (vertical direction) orthogonal to the X-axis direction and the Y-axis direction is the Z-axis direction, and the rotational direction about the Z-axis direction is the θ direction.

A substrate stage 14 constituting a transport table is disposed on the upper surface of the X-axis moving table 12. The substrate stage 14 is a vacuum chucking table, and a color filter substrate (referred to as a CF substrate) W composed of a glass substrate is chucked and secured on the upper surface of the table, and the CF substrate W is transported. The substrate stage 14 is supportably secured so as to be capable of being rotated in the θ direction with respect to the X-axis moving table 12 by a stage rotation mechanism 16 shown by a broken line disposed between the X-axis moving table 12 and the substrate stage 14.

Therefore, the substrate stage 14 (CF substrate W) moves in the X-axis direction (main scanning direction) together with the X-axis moving table 12. The substrate stage 14 (CF substrate W) rotates parallel to the θ direction in relation to the plane (XY plane (horizontal plane) of the X-axis moving table 12.

A pair of Y-axis guide rails 18 is arranged so as to straddle the upward direction of the X-axis guide rails 11 in the Y-axis direction. One end of support columns 19a of the pair of Y-axis guide rails 18 is erectly disposed to one side of the upper surface 2a of the base 2, and the other end of support columns 19b is erectly disposed on a floor set at a distance from the base 2. Support columns 19c are erectly disposed to the other side of the upper surface 2a of the base 2. The pair of Y-axis guide rails 18 is arranged in parallel with spacing set in advance in the X-axis direction. In the present embodiment, a position above the base 2 is set as a work area and a position set at a distance from the base 2 is set as a standby area in the pair of Y-axis guide rails 18 that extend parallel in the Y-axis direction.

A plurality (six, in the present embodiment) of carriage plates 21 is disposed so as to be extended across the pair of Y-axis guide rails 18. Each carriage plate 21 is moveably mounted in the sub scanning direction (Y-axis direction) along the pair of Y-axis guide rails 18. The pair of Y-axis guide rails 18 is provided with a Y-axis linear motor M2, and the Y-axis linear motor M2 moves each carriage plate 21 mounted on the pair of Y-axis guide rails 18 in a reciprocating manner in the Y-axis direction via a pneumatic slider (not shown). In other words, each carriage plate 21 is moved in a reciprocating manner between the work area and the standby area on the Y-axis guide rails 18.

A functional-liquid supply unit 22 and a head electrical wiring unit 23 are mounted on the upper surface of the carriage plates 21. The functional-liquid supply unit 22 is a supply circuit device for storing a predetermined amount of the functional liquid F (see FIG. 3(b)) and supplying functional liquid F to each droplet discharge head 40 (see FIGS. 3(a), (b)). The head electrical wiring unit 23 is an electric circuit device for supplying an electric signal for driving each droplet discharge head 40.

As used herein, the functional liquid F is a red, green, and blue filter ink disposed in the frame of the blank matrix formed on the CF substrate W. The functional liquid F becomes red, green, and blue filters when the fluid has dried after being disposed in the frame of the blank matrix formed on the CF substrate W.

Figure 2:
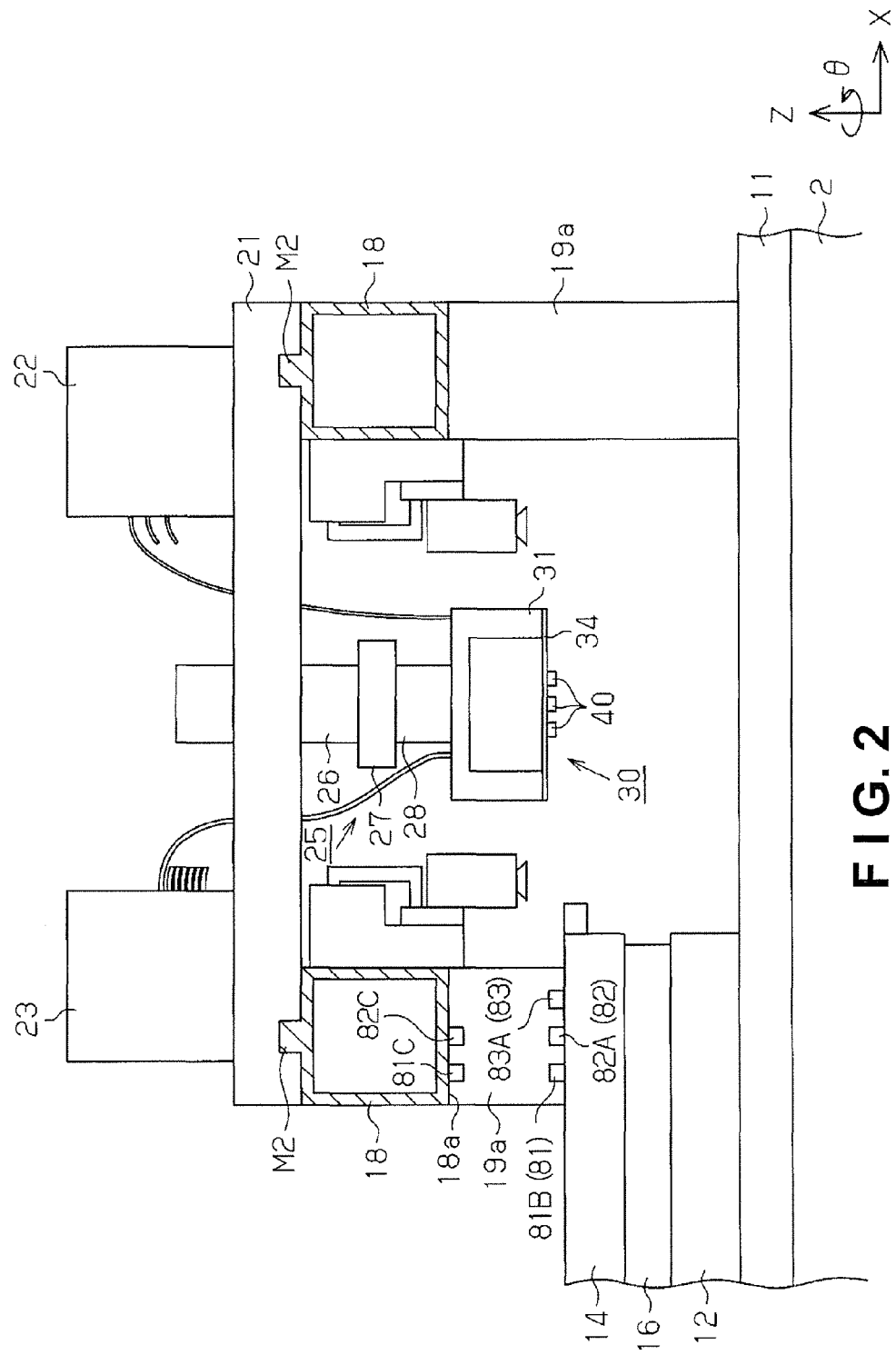
FIG. 2 is a elevational view of the pattern formation device showing the relationship between a carriage plate and a carriage according to the embodiment of the present invention.

A hanging mechanism 25 is disposed in the center position of the lower surface of each carriage plate 21, as shown in FIG. 2, and a carriage 30 is mounted on the lower end part of the hanging mechanism 25.

The hanging mechanism 25 has a hanging substrate 26, a hanging rotation frame 27, and a hanging support frame 28. The hanging substrate 26 is connected and secured in the center position of the lower surface of the carriage plate 21, and the hanging rotation frame 27 is connected to the lower end part of the hanging substrate. The hanging rotation frame 27 connects and supports the hanging support frame 28 on the lower end part of the hanging rotation frame so as to allow rotation in the θ direction. The hanging rotation frame 27 has a θ-axis rotation motor (not shown), and the θ-axis rotation motor is designed to rotate the hanging support frame 28 in the θ-direction in relation to the hanging substrate 26 (carriage plate 21). The carriage 30 is supported and secured by the hanging support frame 28, and the carriage 30 suspended from the hanging mechanism 25 is rotated in the θ direction.

The carriage 30 has a substantially rectangular parallelepiped-shaped carriage frame 31. An aperture part is provided to the two side surfaces in the X-axis direction and the Y-axis direction (the aperture parts in the X-axis direction are not shown), and ambient air can flow in and out of the carriage frame 31. A unit plate 34 is secured using a screw (not shown) or the like to the lower end part of the substantially rectangular parallelepiped-shaped carriage frame 31 of the carriage 30. The droplet discharge head 40 is detachably secured and mounted with good positioning on the unit plate 34. In the present embodiment, two rows of three droplet discharge heads 40 disposed in parallel along the X-axis direction, i.e., a total of six droplet discharge heads 40 are mounted parallel to the Y-axis direction. Tubes, wires, and the like are disposed inside the carriage frame 31 but are not shown in the diagram for the sake of simplicity.

Droplet Discharge Head 40

Next, the droplet discharge head 40 mounted on the unit plate 34 will be described with reference to FIG. 3. FIG. 3(a) is a perspective view of the external appearance of the droplet discharge head 40 as seen from the substrate stage 14. The droplet discharge head 40 is provided with a fluid introduction part 41 having two connection needles 42, a head substrate 43 laterally connected to the fluid introduction part 41, a pump part 44 connected to the fluid introduction part 41, and a nozzle plate 45 connected to the pump part 44.

Tube connection members (not shown) connected to the functional-liquid supply unit 22 are also connected to the connection needles 42 of the fluid introduction part 41. A pair of head connectors 43A is mounted on the head substrate 43 and a flexible flat cable (not shown) connected to the head electrical wiring unit 23 is connected via the head connectors 43A.

On the other hand, a rectangular head main body 40A is composed of the pump part 44 and the nozzle plate 45.

Two nozzle rows 47 composed of discharge nozzles 46 for discharging droplets Fb are formed in a nozzle formation surface 45a of the nozzle plate 45. The two nozzle rows 47 are arranged parallel to each other, and each of the nozzle rows 47 is composed of 180 (schematically represented in the diagram) discharge nozzles 46 aligned in parallel at an equidistant pitch. In other words, two nozzle rows 47 are symmetrically arranged on the nozzle formation surface 45a of the head main body 40A.

FIG. 3(b) shows the interior of the pump part 44 of the droplet discharge head 40; and a cavity 52, a vibration plate 53, and a piezoelectric element PZ are disposed above each discharge nozzle 46. Each cavity 52 is connected to the functional-liquid supply unit 22 via tube connection members (not shown), and stores the functional liquid F (filter ink) from the functional-liquid supply unit 22, and supplies the filter ink to the discharge nozzles 46. The vibration plate 53 causes the volume of the cavity 52 to expand and contract by causing the area facing each cavity 52 to vibrate in the Z direction, and the meniscus of the discharge nozzles 46 is made to vibrate together with the vibration of the vibration plate. When each piezoelectric element PZ receives a predetermined drive waveform signal, the element expands and contracts in the Z direction, whereby each area of the vibration plate 53 is made to vibrate in the Z direction. When the vibration plate 53 of each cavity 52 vibrates in the Z direction, a portion of the stored filter ink is formed into droplets Fb having a predetermined weight and discharged from the discharge nozzles 46.

The base part side of the pump part 44, i.e., the head main body 40A has a flange part 48 formed in the shape of a rectangular flange for receiving the fluid introduction part 41. The flange part 48 acts as a retainer and acts as a connection part that is connected and secured to the unit plate 34 with the aid of head setscrews (not shown). A pair of screw holes (female screws) 49 for small screws for securing the droplet discharge head 40 to the unit plate 34 is formed in the flange part 48. In other words, the droplet discharge head 40 is secured to the unit plate 34 using head setscrews (not shown) that are inserted through the head main body 40A in through-holes formed in predetermined positions of the unit plate 34, inserted through the unit plate 34, and threaded into the screw holes 49.

The X-, Y-, and Z-axes shown in FIGS. 2 and 3 are the same as the X-, Y-, and Z-axes shown in FIG. 1. In other words, the nozzle rows 47 (see FIG. 3(a)) formed in the droplet discharge head 40 in a state in which the unit plate 34 is mounted on the droplet discharge device 1 is configured extending in the Y-axis direction.

Inspection Unit 70

An inspection unit 70 for inspecting droplets discharged from the droplet discharge head 40 will be described next.

The inspection unit 70 is disposed on the pair of X-axis guide rails 11 laid out on the base 2 so as to be capable of moving in the main scanning direction along the pair of X-axis guide rails 11, as shown in FIG. 1.

More specifically, the inspection unit 70 has a moving table 71, and the moving table 71 is mounted so as to be capable of movement in the main scanning direction along the pair of X-axis guide rails 11. The moving table 71 is reciprocally moved in the X-axis direction via a pneumatic slider (not shown) with the aid of an X-axis linear motor M1 provided to the pair of X-axis guide rails 11.

An inspection stand 72 is arranged and secured on the substrate stage 14 side of the upper surface of the moving table 71. The inspection stand 72 has, e.g., a film-coated detection paper P disposed on the upper surface of the inspection stand extending lengthwise along the Y-axis direction. The detection paper P disposed on the inspection stand 72 is designed to have droplets Fb discharged from the discharge nozzles 46 of the droplet discharge head 40 of each carriage 30 land on the paper when the inspection stand 72 is guided directly below the droplet discharge head 40.

Flushing recovery stands 73 are provided in a number (6) equal to the number of carriages 30 in a position adjacent to the inspection stand 72 on the upper surface of the moving table 71, and each of the flushing recovery stands 73 is arranged in parallel along the Y-axis direction.

Droplets Fb are discharged (flushed) from each discharge nozzle 46 of the droplet discharge head 40 of each carriage 30 when each of the flushing recovery stands 73 is guided directly below the corresponding carriage 30, and receptacles 73a of the flushing recovery stands 73 are designed to receive and store the droplets Fb. In other words, flushing is carried out prior to drawing a color filter using the droplets Fb on the CF substrate W, and the droplets Fb based on the flushing are recovered using the flushing recovery stand 73.

Weight-measuring units 74 are provided in a number (6) equal to the number of carriages 30 in a position adjacent to flushing recovery stands 73 arranged in parallel on the upper surface of the moving table 71, and each weight-measuring unit 74 is arranged in parallel along the Y-axis direction.

When guided directly below the corresponding carriage 30, the weight-measuring units 74 are designed to measure the weight of the droplets when droplets Fb discharged from the discharge nozzles 46 of the droplet discharge head 40 of each carriage 30 lands. In other words, the discharge weight of the droplets Fb from each discharge nozzle 46 of the droplet discharge head 40 of each carriage 30 is measured prior to forming a pattern on the CF substrate W using the droplets Fb. In the present embodiment, the inspection stand 72, the flushing recovery stands 73, and the weight-measuring units 74 are disposed so that the upper surfaces thereof are substantially at the same height.

The first and second foreign matter detection sensors 81, 82 for detecting foreign matter deposited on the CF substrate W will be described next.

FIG. 4 is a schematic view showing an arrangement position of each foreign matter detection sensor. The first foreign matter detection sensor 81 is mounted using support columns 19a and 19c of the Y-axis guide rails 18 positioned on the substrate stage 14 side, as shown in FIG. 4.

A first light projecting unit 81A of the first foreign matter detection sensor 81 is disposed inside the support column 19c, has a laser light source (not shown), and emits a first detection light L1 having a predetermined amount of light composed of laser light. A first light receiving unit 81B is provided to the support column 19a so as to face the first light projecting unit 81A, receives the first detection light L1 emitted from the first light projecting unit 81A, and detects the amount of light.

The first light projecting unit 81A has a lower part of the first detection light L1 that faces the side surface Wb of the CF substrate W mounted on the substrate stage 14, and emits the first detection light L1 along the upper surface Wa of the CF substrate W, as shown in FIG. 5. In other words, when foreign matter is deposited on the upper surface Wa of the CF substrate W, the first detection light L1 is blocked by the foreign matter, and the amount of light received by the first light receiving unit 81B is reduced. When foreign matter is deposited on the lower surface Wc of the CF substrate W, the CF substrate W near the deposited foreign matter is in relief with respect to the substrate stage 14. Therefore, the first detection light L1 is blocked and the amount of light received by the first light receiving unit 81B is reduced.

The first light projecting unit 81A causes the optical axis AX1 of the first detection light L1 to slope so as to form a predetermined slope angle θk toward the CF substrate W with respect to horizontal direction. A portion of the first detection light L1 is reflected at the CF substrate W, as shown by an arrow in FIG. 5, by sloping the optical axis AX1 of the first detection light L1, and the reflected first detection light L1 can be made to be incident on the first light receiving unit

81B. In other words, the amount of light of the first detection light L1 incident on the first light receiving unit 81B can be increased. Therefore, the contrast between portions in which foreign matter is not deposited on the CF substrate W and portions in which foreign matter is deposited can be increased in the first light receiving unit 81B for receiving the first detection light L1 when foreign matter is deposited on the CF substrate W. In other words, the effect of the first detection light L1 being diffused can be reduced, and foreign matter deposited on the CF substrate W can be detected with good precision.

A first substrate detection sensor 81C is disposed on the surface 18a facing the upper surface of the substrate stage 14 on the Y-axis guide rails 18 of the substrate stage 14 side, as shown in FIG. 2. The first substrate detection sensor 81C is disposed directly above the optical axis AX1 of the first detection light L1 of the first foreign matter detection sensor 81, and is a sensor for detecting whether the CF substrate W is arranged directly below the optical axis AX1 of the first detection light L1. When the CF substrate W is detected by the first substrate detection sensor 81C to be directly below the optical axis AX1 of the first detection light L1, the first foreign matter detection sensor 81 emits a first detection light L1 from the first light projecting unit 81A.

A second foreign matter detection sensor 82 is disposed in a position adjacent to the first foreign matter detection sensor 81, as shown in FIG. 4. The second foreign matter detection sensor 82 merely has a second light projecting unit 82A provided to the support column 19a and a second light receiving unit 82B provided to the support column 19c so that the direction of the detection light is opposite that of the first foreign matter detection sensor 81. Therefore, a detailed description is omitted.

A second substrate detection sensor 82C is disposed directly above the optical axis of a second detection light L2 emitted from the second light projecting unit 82A (see FIGS. 2 and 4). The second substrate detection sensor 82C is a sensor for detecting whether the CF substrate W is arranged directly below the optical axis of the second detection light L2 of the second foreign matter detection sensor 82 in the same manner as the first substrate detection sensor 81C. The relationship between the second foreign matter detection sensor 82 and the second substrate detection sensor 82C is the same as the relationship between the first foreign matter detection sensor 81 and the first substrate detection sensor 81C. Therefore, a detailed description is omitted.

Next, a third foreign matter detection sensor 83 as a transport table foreign matter detection sensor will be described for detecting foreign matter on the upper surface of the substrate stage 14. The third foreign matter detection sensor 83 is a sensor for detecting foreign matter deposited on the substrate stage 14 as well as tools or the like left behind during maintenance. The third foreign matter detection sensor 83 is disposed in a position adjacent to the second foreign matter detection sensor 82, as shown in FIG. 4, and is provided with a light projecting unit/receiver part 83A having a light projecting unit and a light receiving unit, as well as a reflection plate 83B for reflecting detection light L3 emitted from the light projecting unit of the light projecting unit/receiver 83A to the light receiving unit of the same light projecting unit/receiver 83A.

The light projecting unit of the light projecting unit/receiver 83A has a laser light source (not shown) and causes a detection light L3 having a predetermined amount of light composed of laser light to be emitted toward the reflection plate 83B. The detection light L3 is emitted so as to follow along the upper surface of the substrate stage 14 when the substrate stage 14 passes between the light projecting unit/receiver 83A and the reflection plate 83B. The reflection plate 83B reflects toward the light receiving unit of the light projecting unit/receiver 83A the detection light L3 emitted from the light projecting unit of the light projecting unit/receiver 83A. The light receiving unit of the light projecting unit/receiver 83A receives the detection light L3 reflected at the reflection plate 83B, and detects the amount of the detection light. In other words, the detection light L3 is blocked when foreign matter is present on the upper surface of the substrate stage 14, and the amount of light received by the light receiving unit of the light projecting unit/receiver 83A is reduced.

A fourth foreign matter detection sensor 84 as an inspection unit foreign matter detection sensor for detecting foreign matter in the inspection unit 70 will be described next.

The fourth foreign matter detection sensor 84 is a device for detecting foreign matter deposited on the upper surface of the inspection stand 72, the flushing recovery stands 73, and the weight-measuring units 74 of the inspection unit 70, an increase in elevation of a detection paper P of the inspection stand 72, as well as tools and the like left behind during maintenance.

The fourth foreign matter detection sensor 84 is provided with a light projecting unit/receiver 84A having a light projecting unit and a light receiving unit, and a reflection plate 84B for reflecting to the light receiving unit of the light projecting unit/receiver 84A a detection light L4 emitted from the light projecting unit of the light projecting unit/receiver 84A, in the same manner as the third foreign matter detection sensor 83. The light projecting unit/receiver 84A of the fourth foreign matter detection sensor 84 is provided so as to have a predetermined height with the aid of a securing member 85a disposed in a position adjacent to the support column 19a of the pair of Y-axis guide rails 18 of the inspection unit 70 side, as shown in FIG. 1. The reflection plate 84B is disposed so as to face the light projecting unit/receiver 84A with the aid of a securing member 85b disposed in a position adjacent to the support column 19c of the pair of Y-axis guide rails 18 of the inspection unit 70 side.

The light projecting unit of the light projecting unit/receiver 84A has a laser light source (not shown), and a detection light L4 having a predetermined amount of light composed of laser light is emitted toward the reflection plate 84B. The detection light L4 is emitted so as to follow along the upper surface of the inspection stand 72, the flushing recovery stands 73, and the weight-measuring units 74 of the inspection unit 70 when the inspection unit 70 passes between the light projecting unit/receiver 84A and the reflection plate 84B. The reflection plate 84B reflects toward the light receiving unit of the light projecting unit/receiver 84A a detection light L4 emitted from the light projecting unit of the light projecting unit/receiver 84A. The light receiving unit of the light projecting unit/receiver 84A receives the detection light L4 reflected at the reflection plate 84B, and detects the amount of detection light. In other words, the detection light L4 is blocked when foreign matter is present on the upper surface of the inspection unit 70 and the amount of light received by the light receiving unit of the light projecting unit/receiver 84A is reduced.

Next, the electrical configuration of the droplet discharge device 1 will be described with reference to FIG. 6. FIG. 6 is an electrical block diagram showing the electrical configuration of the droplet discharge device 1.

In FIG. 6, a control device 100 has a CPU 101, a ROM 102, a RAM 103, and the like. The control device 100 carries out processing for transporting the X-axis moving table 12, processing for transporting each carriage plate 21, processing for discharging droplets of each droplet discharge head 40 disposed in each carriage 30, and other processing in accordance with various stored data and control programs. The control device 100 also carries out processing and the like for detecting foreign matter on the CF substrate W, the substrate stage 14, and the inspection unit 70.

An I/O device 104 having various operating switches and a display is connected to the control device 100. The I/O device 104 displays the processing state of various processes carried out by the droplet discharge device 1. The I/O device 104 generates image data (bitmap data BD) for forming a pattern on the CF substrate W using the droplets Fb, and the bitmap data BD is inputted to the control device 100. The control device 100 stores the inputted bitmap data BD in the RAM 103.

The bitmap data BD is data that specifies whether to switch on or off the piezoelectric element PZ in accordance with the value of each bit (0 or 1). The bitmap data BD is data that specifies whether droplets Fb are to be discharged or not in each position of the CF substrate W specified in advance when the CF substrate W passes directly below the droplet discharge head 40 (each discharge nozzle 46)

In other words, the bitmap data BD is data the specifies whether to discharge the droplets Fb or not in arranged positions, being prepared for forming a color filter pattern for each outward movement and return movement when the CF substrate is reciprocated many times directly below the droplet discharge head 40 (each discharge nozzle 46) in order to form a color filter pattern on the CF substrate W using the droplets Fb.

More specifically, a color filter pattern is drawn on the CF substrate W when the droplets Fb are discharged using the bitmap data BD that corresponds to each outward movement and each return movement, being prepared for each outward movement and inward movement of the X-axis moving table 12 (CF substrate W) directly below the droplet discharge head 40 (each discharge nozzle 46).

In the present embodiment, the pattern for drawing on the CF substrate W is calculated using a pre-design or the like, and the bitmap data BD is created from the calculated pattern.

An X-axis linear motor drive circuit 105 is connected to the control device 100. The control device 100 outputs a drive control signal to the X-axis linear motor drive circuit 105. The X-axis linear motor drive circuit 105 drives an X-axis linear motor M1 for moving the X-axis moving table 12 (CF substrate W) in response to the drive control signal from the control device 100. The control device 100 outputs to the X-axis linear motor drive circuit 105 the drive control signal for moving the inspection unit 70 in the case that the droplets Fb are inspected by the inspection unit 70. The X-axis linear motor drive circuit 105 drives the X-axis linear motor M1 for moving the moving table 71 in response to the drive control signal for moving the inspection unit 70 from the control device 100.

A Y-axis linear motor drive circuit 106 is connected to the control device 100. The control device 100 outputs a drive control signal to the Y-axis linear motor drive circuit 106. The Y-axis linear motor drive circuit 106 drives a Y-axis linear motor M2 for moving each carriage plate 21 in response to the drive control signal from the control device 100.

A head drive circuit 108 provided to each droplet discharge head 40 is connected to the control device 100. The control device 100 outputs to the head drive circuit 108 a discharge-timing signal LT synchronized to a predetermined discharge frequency. The control device 100 synchronizes a drive voltage COM for driving each piezoelectric element PZ with a predetermined discharge frequency, and provides output to the corresponding head drive circuit 108.

The control device 100 generates a pattern-forming control signal SI synchronized with a predetermined frequency using the bitmap data BD, and serially transfers to the head drive circuit 108 the pattern-forming control signal SI. The head drive circuit 108 associates the pattern-forming control signal SI from the control device 100 with each piezoelectric element PZ and sequentially performs serial/parallel conversion. Each time a discharge timing signal LT is received from the control device 100, the head drive circuit 108 latches the pattern-forming control signal SI that has been converted in series or in parallel, and supplies a drive voltage COM to each piezoelectric element PZ selected by the pattern-forming control signal SI.

A substrate detection sensor drive circuit 110 is connected to the control device 100. The control device 100 outputs a control drive signal to the substrate detection sensor drive circuit 110. The substrate detection sensor drive circuit 110 drives the first substrate detection sensor 81C and the second substrate detection sensor 82C in response to drive control signals from the control device 100. The substrate detection sensor drive circuit 110 outputs to the control device 100 detection signals Sa, Sb when the CF substrate W is detected to be positioned directly below the optical axis of the detection lights that correspond to the first and second substrate detection sensors 81C, 82C. In the present embodiment, the first and second substrate detection sensors 81C, 82C are constantly driven and controlled during movement of the droplet discharge device 1.

A first foreign matter detection sensor drive circuit 111 is connected to the control device 100. The control device 100 as foreign matter detection sensor control unit outputs a drive control signal to the first foreign matter detection sensor drive circuit 111 when the detection signal Sa is inputted from the first substrate detection sensor 81C. The first foreign matter detection sensor drive circuit 111 emits a first detection light L1 from the first light projecting unit 81A in response to a drive control signal from the control device 100. The first foreign matter detection sensor drive circuit 111 outputs to the control device 100 a detection value indicating the amount of light received by the first light receiving unit 81B of the first foreign matter detection sensor 81. The control device 100 receives the detection results from the first foreign matter detection sensor 81, and compares the detection value from the first foreign matter detection sensor 81 and a first threshold value set in advance in the ROM 102. The control device 100 determines that foreign matter is deposited on the CF substrate W when the detection value from the first foreign matter detection sensor 81 is less than the first threshold value, drives and controls the X-axis linear motor M1 to immediately stop the transport operation of the substrate stage 14 (X-axis moving table 12), and switches on a warning lamp (not shown) provided to the I/O device 104.

A second foreign matter detection sensor drive circuit 112 is connected to the control device 100. The control device 100 as foreign matter detection sensor control unit outputs a drive control signal to the second foreign matter detection sensor drive circuit 112 when the detection signal Sb is inputted from the second substrate detection sensor 82C. The second foreign matter detection sensor drive circuit 112 emits the second detection light L2 from the second light projecting unit 82A in response to the drive control signal from the control device 100. The second foreign matter detection sensor drive circuit 112 outputs to the control device 100 a detection value indicating the amount of light received by the second light receiving unit 82B of the second foreign matter detection sensor 82. The control device 100 receives the detection results from the second foreign matter detection sensor 82, and compares the detection value from the second foreign matter detection sensor 82 and the first threshold value. The control device 100 determines that foreign matter is deposited on the CF substrate W when the detection value from the second foreign matter detection sensor 82 is less than the first threshold value, drives and controls the X-axis linear motor M1 to immediately stop the transport operation of the substrate stage 14 (X-axis moving table 12), and switches on a warning lamp (not shown) provided to the I/O device 104.

A third foreign matter detection sensor drive circuit 113 is connected to the control device 100. The control device 100 outputs a drive control signal to the third foreign matter detection sensor drive circuit 113. The third foreign matter detection sensor drive circuit 113 drives the third foreign matter detection sensor 83 in response to a drive control signal from the control device 100, and emits a detection light L3 from the light projecting unit of the light projecting unit/receiver 83A. The third foreign matter detection sensor drive circuit 113 outputs to the control device 100 a detection value indicating the amount of light received by the light receiving unit of the light projecting unit/receiver 83A. The control device 100 receives the detection results from the third foreign matter detection sensor drive circuit 113, and compares the detection value from the third foreign matter detection sensor 83 and a second threshold value set in advance in the ROM 102. The control device 100 determines that foreign matter is present on the substrate stage 14 when the detection value from the third foreign matter detection sensor 83 is less than the second threshold value, drives and controls the X-axis linear motor M1 to immediately stop the transport operation of the substrate stage 14 (X-axis moving table 12), and switches on a warning lamp (not shown) provided to the I/O device 104. In the present embodiment, the control device 100 constantly drives the third foreign matter detection sensor 83 during movement of the droplet discharge device 1.

A fourth foreign matter detection sensor drive circuit 114 is connected to the control device 100. The control device 100 outputs a drive control signal to the fourth foreign matter detection sensor drive circuit 114. The fourth foreign matter detection sensor drive circuit 114 drives a fourth foreign matter detection sensor 84 in response to a drive control signal from the control device 100, and emits a detection light L4 from the light projecting unit of the light projecting unit/receiver 84A. The fourth foreign matter detection sensor drive circuit 114 outputs to the control device 100 a detection value indicating the amount of light received by the light receiving unit of the light projecting unit/receiver 84A. The control device 100 receives the detection results from the fourth foreign matter detection sensor drive circuit 114, and compares the detection value from the fourth foreign matter detection sensor 84 and the second threshold value. The control device 100 determines that foreign matter is present on the inspection unit 70 when the detection value from the fourth foreign matter detection sensor 84 is less than the second threshold value, drives and controls the X-axis linear motor M1 to immediately stop the transport operation of the moving table 71, and switches on a warning lamp (not shown) provided to the I/O device 104. In the present embodiment, the control device 100 constantly drives the fourth foreign matter detection sensor 84 during movement of the droplet discharge device 1.

A method for detecting foreign matter on a droplet discharge device 1 configured in the manner described above will be described next.

Below, the droplet discharge device 1 forms a pattern on the CF substrate W newly disposed on the substrate stage 14.

The control device 100 drives the X-axis linear motor M1 and moves the substrate stage 14 (X-axis moving table 12) in the X-axis direction. The first substrate detection sensor 81C eventually detects the CF substrate W and outputs the detection signal Sa to the control device 100. The control device 100 drives the first foreign matter detection sensor 81 via the first foreign matter detection sensor drive circuit 111 when the detection signal Sa is inputted, and emits the first detection light L1 from the first light projecting unit 81A toward the first light receiving unit 81B. The first light receiving unit 81B outputs to the control device 100 the detection value of the received first detection light L1 via the first foreign matter detection sensor drive circuit 111. The control device 100 compares the detection value from the first foreign matter detection sensor 81 and the first threshold value set in advance in the ROM 102, and detects foreign matter deposited on the CF substrate W.

The second substrate detection sensor 82C subsequently detects the CF substrate W, and outputs the detection signal Sb to the control device 100. The control device 100 drives the second foreign matter detection sensor 82 when the detection signal Sb is inputted, and emits the second detection light L2 from the second light projecting unit 82A toward the second light receiving unit 82B. The second light receiving unit 82B outputs to the control device 100 the detection value of the received second detection light L2 via the second foreign matter detection sensor drive circuit 112. The control device 100 compares the detection value from the second foreign matter detection sensor 82 and the first threshold value set in advance in the ROM 102, and detects foreign matter deposited on the CF substrate W.

The first and second substrate detection sensors 81C, 82C stop output of the detection signals Sa, Sb to the control device 100 when the CF substrate W is no longer detected to be directly below, and the control device 100 stops the first and second foreign matter detection sensors 81, 82 via the first and second foreign matter detection sensor drive circuits 111, 112.

In this case, the first detection light L1 emitted from the first light projecting unit 81A of the first foreign matter detection sensor 81 is diffused in approach to the first light receiving unit 81B, and the accuracy for detecting foreign matter deposited on the CF substrate W is reduced. However, the second foreign matter detection sensor 82 can detect foreign matter with good precision in areas in which detection accuracy of the first foreign matter detection sensor 81 is reduced by having provided a second foreign matter detection sensor 82 in which the direction of the detection light is opposite from that of the first foreign matter detection sensor 81. In other words, foreign matter can be detected with good precision in the entire area of the CF substrate W by the cooperative operation of the first and second foreign matter detection sensors 81, 82.

When the CF substrate W is not positioned directly below the optical axes of the first and second detection lights L1, L2, a portion of the first and second detection lights L1, L2 is reflected at the CF substrate W and cannot be inputted to the first and second light receiving units 81B, 82B. Therefore, the amount of light received by the first and second light receiving units 81B, 82B is reduced. In this case, the detection value indicating the amount of light received by the first and second light receiving units 81B, 82B falls below the first threshold value, and the control device 100 errantly detects that foreign matter is deposited on the CF substrate W. However, errant detection of foreign matter can be prevented due to the reduction in the amount of light by providing the first and second substrate detection sensors 81C, 82C.

The control device 100 constantly drives the third foreign matter detection sensor 83 via the third foreign matter detection sensor drive circuit 113, and causes detection light L3 to be emitted from the light projecting unit of the light projecting unit/receiver 83A of the third foreign matter detection sensor 83. The light projecting unit/receiver 83A receives the detection light L3 reflected at the reflection plate 83B in the light receiving unit of the light projecting unit/receiver 83A, and outputs the detection value to the control device 100 via the third foreign matter detection sensor drive circuit 113. The control device 100 compares the detection value from the third foreign matter detection sensor 83 and the second threshold value set in advance in the ROM 102, and detects foreign matter deposited on the substrate stage 14 as well as tools or the like left behind during maintenance.

In other words, the first and second foreign matter detection sensors 81, 82 detect foreign matter deposited on the CF substrate W, and the third foreign matter detection sensor 83 detects foreign matter deposited on upper surface of the substrate stage 14 as well as tools or the like left behind during maintenance. Therefore, foreign matter deposited on the CF substrate W, foreign matter deposited on the substrate stage 14, and tools or the like left behind during maintenance can be detected prior to moving the substrate stage 14 mounted on the CF substrate W directly below the carriage 30. As a result, damage to the carriage 30 (droplet discharge head 40) and the CF substrate W caused by the above factors can be prevented.

The control device 100 drives the X-axis linear motor M1 and transports the moving table 71 of the inspection unit 70 in the reverse X-axis direction when droplets discharged from the droplet discharge head 40 are to be inspected. The control device 100 constantly drives the fourth foreign matter detection sensor 84 via the fourth foreign matter detection sensor drive circuit 114, and causes detection light L4 to be emitted from the light projecting unit of the light projecting unit/receiver 84A of the fourth foreign matter detection sensor 84. The light projecting unit/receiver 84A receives the detection light L4 reflected by the reflection plate 84B in the light receiving unit of the light projecting unit/receiver 84A, and outputs the detection value to the control device 100 via the fourth foreign matter detection sensor drive circuit 114. The control device 100 compares the detection value from the fourth foreign matter detection sensor 84 and the second threshold value set in advance in the ROM 102, and detects foreign matter deposited on the upper surfaces of the inspection stand 72, the flushing recovery stand 73, and the weight-measuring units 74 of the inspection unit 70, an increase in elevation of a detection paper P of the inspection stand 72, as well as tools and the like left behind during maintenance.

Therefore, it is possible to detect foreign matter deposited on the upper surfaces of the inspection stand 72, the flushing recovery stand 73, and the weight-measuring units 74 of the inspection unit 70, an increase in elevation of a detection paper P of the inspection stand 72, as well as tools and the like left behind during maintenance prior to moving the inspection unit 70 directly below the carriage 30 (droplet discharge head 40). As a result, damage to the carriage 30 (droplet discharge head 40) due to the factors described above can be prevented.

In accordance with the embodiment described above, effects such as those described below can be obtained.

(1) In accordance with the embodiment described above, a first foreign matter detection sensor 81 is provided for emitting a first detection light L1 from a first light projecting unit 81A provided to a support column 19c of the pair of Y-axis guide rails 18 of the substrate stage 14 side, to a first light receiving unit 81B that is provided to a support column 19a. Also, a second foreign matter detection sensor 82 is provided for emitting a second detection light L2 from a second light projecting unit 82A provided to the support column 19a to a second light receiving unit 82B provided to the support column 19c so that the direction of the detection light is opposite that of the first foreign matter detection sensor 81. The control device 100 drives and controls the X-axis linear motor M1 and immediately stops the transport operation of the substrate stage 14 (X-axis moving table 12) when foreign matter is detected on the CF substrate W.

Therefore, the first detection light L1 of the first foreign matter detection sensor 81 is diffused, and the second foreign matter detection sensor 82 in which the direction of the detection light is opposite can detect with good precision foreign matter deposited in an area in which the precision of detecting foreign matter deposited on the CF substrate W is reduced. In other words, foreign matter can be detected with good precision in the entire area of the CF substrate W by the cooperative operation of the first and second foreign matter detection sensors 81, 82. As a result, damage to the carriage 30 (droplet discharge head 40) caused by foreign matter deposited on the CF substrate W can be prevented.

(2) In accordance with the embodiment described above, the optical axis AX1 of the first detection light L1 emitted from the first light projecting unit 81A of the first foreign matter detection sensor 81 is sloped toward the CF substrate W. Similarly, the optical axis of the second detection light L2 emitted from the second light projecting unit 82A of the second foreign matter detection sensor 82 is sloped toward the CF substrate W.

Therefore, a portion of the first and second detection lights L1, L2 emitted from the first and second light projecting units 81A, 82A is reflected to the CF substrate W, whereby the amount of light received by the first and second light receiving units 81B, 82B can be increased. As a result, the contrast between the portions in which foreign matter is not deposited on the CF substrate W and portions in which foreign matter is deposited can be increased in the first and second light receiving units 81B, 82B for receiving the first and second detection lights L1, L2 when foreign matter is deposited on the CF substrate W. In other words, the effect of the detection light being diffused can be reduced, and foreign matter deposited on the CF substrate W can be detected with good precision.

(3) In accordance with the embodiment described above, a first substrate detection sensor 81C is provided for detecting that the CF substrate W is disposed directly below the optical axis AX1 of the first detection light L1 emitted from the first light projecting unit 81A of the first foreign matter detection sensor 81. Similarly, a second substrate detection sensor 82C is provided for detecting that the CF substrate W is disposed directly below the optical axis of the second detection light L2 emitted from the second light projecting unit 82A of the second foreign matter detection sensor 82. The control device 100 causes detection light to be emitted from the each of the first and second light projecting units 81A, 82A when the first and second substrate detection sensors 81C, 82C detect the CF substrate W.

Therefore, the CF substrate W can always be positioned directly below the optical axis of the first and second detection lights L1, L2 when the first and second foreign matter detection sensors 81, 82 are emitting first and second detection lights L1, L2. As a result, the control device 100 can be prevented from making an errant detection of foreign matter deposited on the CF substrate W when a portion of the first and second detection lights L1, L2 cannot be reflected at the CF substrate W and the amount of light received by the first and second light receiving units 81B, 82B is reduced.

(4) In accordance with the embodiment described above, a third foreign matter detection sensor 83 is provided for detecting foreign matter deposited on the substrate stage 14 or tools or other foreign matter left behind on the substrate stage 14 during maintenance. Also, the control device 100 drives and controls the X-axis linear motor M1 and immediately stops the transport operation of the substrate stage 14 (X-axis moving table 12) when foreign matter has been detected on the substrate stage 14.

Therefore, the first and second foreign matter detection sensors 81, 82 detect foreign matter deposited on the CF substrate W, and the third foreign matter detection sensor 83 can detect foreign matter deposited on the substrate stage 14 or tools or other foreign matter left behind on the substrate stage 14 during maintenance. As a result, damage to the carriage 30 (droplet discharge head 40) caused by foreign matter can be more reliably prevented prior to the substrate stage 14 on which the CF substrate W is mounted being moved directly below the carriage 30.

(5) In accordance with the embodiment described above, a fourth foreign matter detection sensor 84 was provided for detecting foreign matter deposited on the inspection stand 72, the flushing recovery stand 73, and the weight-measuring units 74 of the inspection unit 70; an increase in elevation of a detection paper P of the inspection stand 72; as well as tools and the like left behind during maintenance. Also, the control device 100 drives and controls the X-axis linear motor M1 and immediately stops the transport operation of the moving table 71 when foreign matter is detected on the inspection unit 70.

Therefore, it is possible to detect foreign matter on the inspection unit 70, an increase in elevation of a detection paper P of the inspection stand 72, as well as tools and the like left behind during maintenance of the inspection unit 70 prior to moving the inspection unit 70 directly below the carriage 30 (droplet discharge head 40). As a result, damage to the carriage 30 (droplet discharge head 40) due to the factors described above can be more reliably prevented.

The embodiment described above can be modified in the manner described below.

In the embodiment described above, the light projecting unit/receiver 84A of the fourth foreign matter detection sensor 84 for detecting foreign matter on the inspection unit 70 is provided to the securing member 85a, and the reflection plate 84B is provided to the securing member 85b. No limitation is imposed thereby, and the light projecting unit/receiver 84A and the reflection plate 84B may be provided to the support column 19a and the support column 19c of the pair of Y-axis guide rails 18 of the inspection unit 70 side.

In the embodiment described above, the optical axes of the first and second detection lights L1 and L2 are sloped and toward the CF substrate W. No limitation is imposed thereby, and the detection lights may be emitted so as to be parallel to the upper surface of the CF substrate W, for example.

In the embodiment described above, an example of a droplet discharge device 1 was shown as a droplet discharge device in which filter ink is formed into droplets and discharged to form a color filter on a CF substrate. No limitation is imposed thereby, and application can also be made to a droplet discharge device for forming metal wiring, a droplet discharge device for forming an insulating layer, a droplet discharge device for forming a liquid crystal layer and an alignment film, a droplet discharge device for forming a light-emitting layer of an organic EL display device, and other pattern formation devices.

In the embodiment described above, an example of a droplet discharge device 1 was shown in which six carriages 30 having six droplet discharge heads 40 are mounted in the device. No limitation is imposed thereby, and the arrangement and number of droplet discharge heads mounted in a carriage, and the number of carriages mounted in the droplet discharge device can be suitably modified.

General Interpretation of Terms

In understanding the scope of the present invention, the term "configured" as used herein to describe a component, section or part of a device includes hardware and/or software that is constructed and/or programmed to carry out the desired function. In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A droplet discharge device comprising:
    a transport table configured and arranged to transport a substrate mounted on the transport table along a transport path;
    a droplet discharge head configured and arranged to discharge a functional liquid onto the substrate mounted on the transport table; and
    a first foreign matter detection sensor configured and arranged to detect foreign matter on the substrate, the first foreign matter detection sensor having a first light projecting unit and a first light receiving unit,
        the first light projecting unit being configured and arranged to emit a first detection light so that an optical axis of the first detection light is sloped toward the substrate, and
        the first light receiving unit being disposed across the transport path from the first light projecting unit, and configured and arranged to receive a part of the first detection light emitted directly to the first light receiving unit along an upper surface of the substrate and a part of the first detection light reflected by the upper surface of the substrate,
    the first foreign matter detection sensor detecting foreign matter on the substrate based on an amount of the first detection light received by the first light receiving unit.

2. The droplet discharge device according to claim 1, further comprising
  a first substrate detection sensor configured and arranged to detect that the substrate is positioned directly below an optical axis of the first detection light, and
  a foreign matter detection sensor control unit configured to control an operation of the first foreign matter detection sensor based on a detection signal from the first substrate detection sensor.

3. The droplet discharge device according to claim 1, further comprising
  a transport table foreign matter detection sensor configured and arranged to detect foreign matter on an upper surface of the transport table.

4. The droplet discharge device according to claim 1, wherein
  an inspection unit configured and arranged to reciprocally move in a main scanning direction along the transport path independent from the transport table directly below the droplet discharge head to inspect conditions of the droplets discharged from the droplet discharge head, and
  an inspection unit foreign matter detection sensor configured and arranged to detect foreign matter in the inspection unit.

5. A droplet discharge device comprising:
  a transport table configured and arranged to transport a substrate mounted on the transport table along a transport path;
  a droplet discharge head configured and arranged to discharge a functional liquid onto the substrate mounted on the transport table;
  a first foreign matter detection sensor configured and arranged to detect foreign matter on the substrate, the first foreign matter detection sensor having a first light projecting unit and a first light receiving unit,
    the first light projecting unit being configured and arranged to emit a first detection light, and
    the first light receiving unit being disposed across the transport path from the first light projecting unit, and configured and arranged to receive a part of the first detection light emitted directly to the first light receiving unit along an upper surface of the substrate and a part of the first detection light reflected by the upper surface of the substrate; and
  a second foreign matter detection sensor configured and arranged to detect foreign matter on the substrate, the second foreign matter detection sensor having a second light projecting unit and a second light receiving unit,
    the second light projecting unit being configured and arranged to emit a second detection light, and
    the second light receiving unit being disposed across the transport path from the second light projecting unit, and configured and arranged to receive a part of the second detection light emitted directly to the second light receiving unit along the upper surface of the substrate and a part of the second detection light reflected by the upper surface of the substrate,
  the first foreign matter detection sensor detecting foreign matter on the substrate based on an amount of the first detection light received by the first light receiving unit,
  the second foreign matter detection sensor detecting foreign matter on the substrate based on an amount of the second detection light received by the second light receiving unit,
  the first light projecting unit and the second light projecting unit being disposed on opposite sides of the transport path.

6. The droplet discharge device according to claim 5, wherein
  the second foreign matter detection sensor is arranged so that an optical axis of the second detection light is sloped toward the substrate.

7. The droplet discharge device according to claim 5, further comprising
  a second substrate detection sensor configured and arranged to detect that the substrate is positioned directly below an optical axis of the second detection light, and
  the foreign matter detection sensor control unit being further configured to control an operation of the second foreign matter detection sensor based on a detection signal from the second substrate detection sensor.

* * * * *